United States Patent [19]

Terry et al.

[11] Patent Number: 4,474,889
[45] Date of Patent: Oct. 2, 1984

[54] MINIATURE GAS CHROMATOGRAPH APPARATUS

[75] Inventors: Stephen C. Terry; John H. Jerman, both of Palo Alto, Calif.

[73] Assignee: Microsensor Technology Inc., Fremont, Calif.

[21] Appl. No.: 371,617

[22] Filed: Apr. 26, 1982

[51] Int. Cl.³ .................... G01N 31/08; B01D 53/00
[52] U.S. Cl. .................... 436/161; 55/386; 73/23.1; 422/89
[58] Field of Search .............. 73/23.1; 55/197, 386; 422/83, 89; 436/161

[56] References Cited

U.S. PATENT DOCUMENTS

| | | | |
|---|---|---|---|
| 3,138,025 | 6/1964 | Fingerson | 73/339 |
| 3,138,948 | 6/1964 | Pfefferle | 73/27 |
| 3,333,470 | 8/1967 | Fingerson | 73/362 |
| 3,538,744 | 11/1970 | Karasek | 73/23.1 |
| 3,633,426 | 1/1972 | Broerman | 73/422 |
| 3,911,386 | 10/1975 | Beaudoin et al. | 338/34 |
| 4,033,169 | 7/1977 | Fujishiro et al. | 73/23 |
| 4,142,400 | 3/1979 | Colla et al. | 73/23 |
| 4,241,019 | 12/1980 | Nakatani et al. | 422/94 |
| 4,359,891 | 11/1982 | Ahlstrom | 73/23.1 |

OTHER PUBLICATIONS

Terry, Steven C. et al., IEEE Trans. Electron Devices, vol. Ed.-26, No. 12, 1880-1886 (Dec. 1979).
Chemical Abstracts, 90: 97088d (1979).
S. C. Terry et al., Theory, Des., Biomed. Appl. Solid State Chem. Sens., Workshop 1977 (Pub. 1978), 207-218 (Eng), edited by Cheung, Peter W.; Fleming, David G.; Neuman, Michael R., CRC: West Palm Beach, Fla.
"A Feasibility Study of a Pocket-Sized Gas Chromatographic Air Analyzer" by Stephen C. Terry & John H. Jerman; Jul. 1977.
"A Prototype Gas Analysis System Using a Miniature Gas Chromatograph" by James B. Angell, et al., Apr. 1981.
"A Prototype Gas Analysis System Using a Miniature Gas Chromatograph" by John H. Jerman, et al., Jun. 1, 1980.
"Developments in Micro Gas Chromatography" by W. F. Wilhite, J. of G.C.-Feb. 1966, p. 47.
"A New Detector for Gaseous Components Using Semiconductive Thin Films", Analytical Chemistry, vol. 34, No. 11, Oct. 1962.
"Vacuum Ultraviolet Photochemistry in Thin Resist Films" by Paul W. Bohn & James W. Taylor, Analytical Chemistry, vol. 53, No. 7, Jun. 1981, pp. 1082-1087.
"Study on a Detector for Gaseous Components Using Semiconductive Thin Films", vol. 38, No. 8, Jul. 1966.

Primary Examiner—Sidney Marantz
Attorney, Agent, or Firm—Limbach, Limbach & Sutton

[57] ABSTRACT

A gas chromatography assembly has a substrate wafer with grooves and a valve seat etched therein. A plate cooperates with the wafer and the grooves to define gas channels: a carrier gas channel and a sample gas channel, each passing through the valve seat. A valve actuator is attached to the valve seat for controlling the flow of sample gas from the sample gas channel into the carrier gas channel. A pump is attached to the wafer and is connected to the sample gas channel. The pump cooperates with the valve actuator to inject sample gas from the sample gas channel into the carrier gas channel. A modular capillary tube and a detector are connected to the carrier gas channel to analyze the properties of the sample gas flowing in the carrier gas channel from the sample gas channel.

24 Claims, 7 Drawing Figures

FIG_1.

FIG_5.

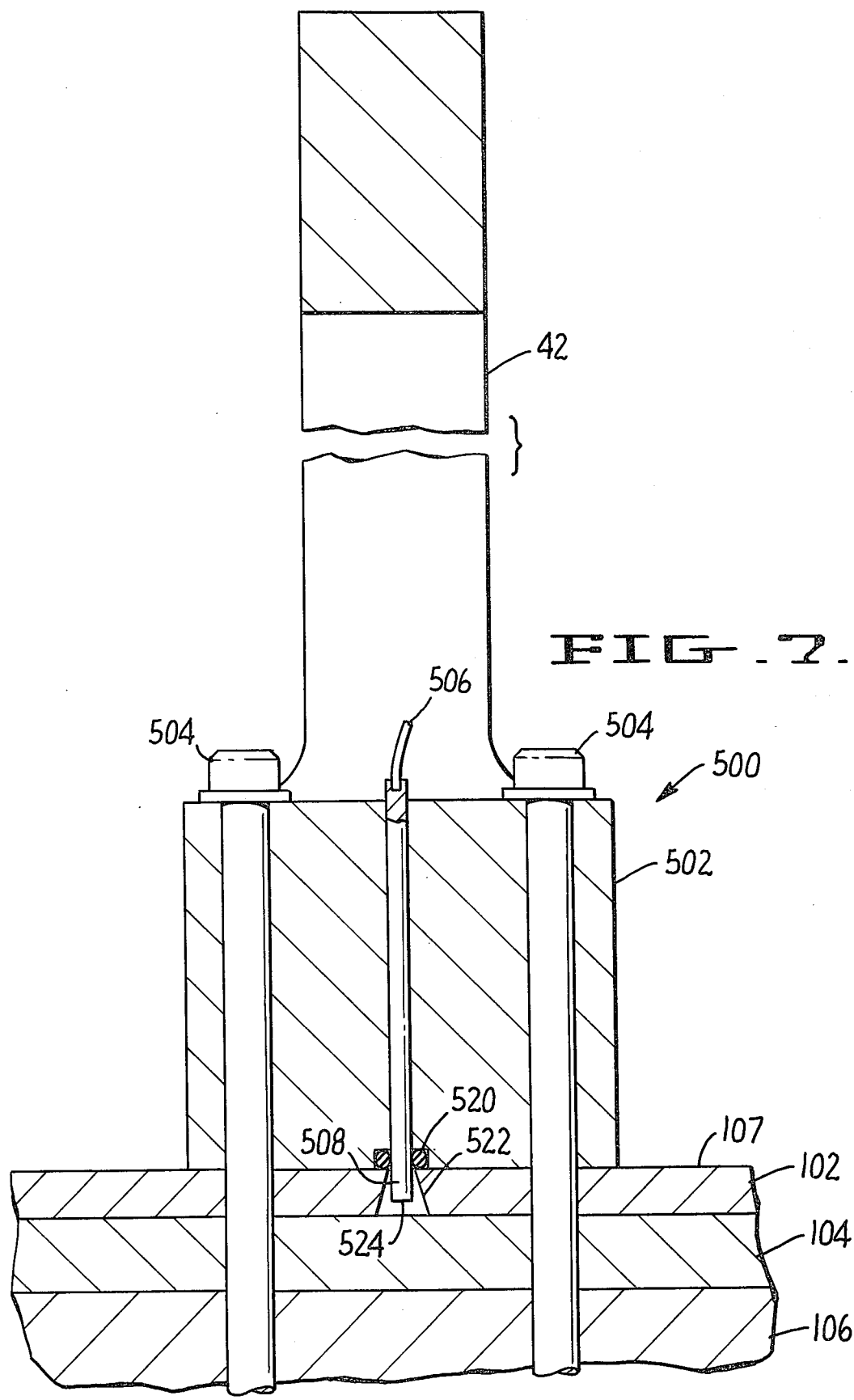

MINIATURE GAS CHROMATOGRAPH APPARATUS

BACKGROUND OF THE INVENTION

The present invention relates to a miniature gas chromatograph apparatus and, more particularly, to one which uses a substrate wafer with grooves etched by techniques from integrated circuit technology.

The technology of gas chromatography is well-known in the art. In recent years, however, there has been great development in the field of gas chromatography in which the etching technology that is used to make integrated circuit devices is used to etch the gas channels in a semi-conductor substrate wafer. With this technology, the size of gas channels in a substrate wafer can be reduced, thereby making miniaturized gas chromatography systems possible.

In a report entitled "A Feasibility Study Of A Pocket-Size Gas Chromatographic Air Analyzer" dated July 1977, prepared under the National Institute For Occupational Safety And Health Contract NIOSH2100-76-0140, a pocket-size gas chromatograph apparatus is disclosed. The present invention is an improvement over that device.

SUMMARY OF THE INVENTION

Therefore, in accordance with the present invention, there is provided a substrate wafer which has a carrier gas groove means, a valve seat means connected to the carrier gas groove means for controlling the flow of gas therethrough, and a sample gas groove means which also passes through the valve seat means. A plate cooperates with the wafer and the groove means to define gas channels. A valve actuating means is attached to the valve seat means for controlling the flow of gas from the sample gas channel means into the carrier gas channel means. A pump means is attached to the wafer, connected to the sample gas channel means with the pump cooperating with the valve actuating means for injecting sample gas from the sample gas channel means into the carrier gas channel means. A modular capillary tube means is attached to the wafer, one end of which is connected to the carrier gas channel means. A detector means is connected to the other end of the capillary tube means for measuring properties of gas flowing from the capillary tube means.

The present invention is also an improvement to a gas chromatography system, which has a carrier gas channel means, a valve means, with the carrier gas channel means passing through the valve means, a sample gas channel means, and with the sample gas channel means also passing through the valve means. The valve means is for controlling the flow of gas from the sample gas channel means into the carrier gas channel means. A capillary tube means is connected to the carrier gas channel means. A detector means is connected to the capillary tube means for measuring the properties of the gas flowing from the capillary tube means. The improvement of the present invention comprises a pump means which is connected to the sample gas channel means. The pump means cooperates with the valve means to inject gas from the sample gas channel means through the valve means into the carrier gas channel means. The volume of the sample gas channel means between the valve means and the pump means is such that no gas from the pump means is injected into the carrier gas channel means.

Finally, the present invention is directed to a miniature valve apparatus, a miniature gas injection pump apparatus, and a miniature coupling device for fitting an external tube to a gas channel in a substrate wafer.

DESCRIPTION OF THE DRAWINGS

FIG. 7 is a partial cross-sectional side view of the modular capillary tube mounted on the assembly of the present invention.

DETAILED DESCRIPTION OF THE DRAWINGS

Figure 1:
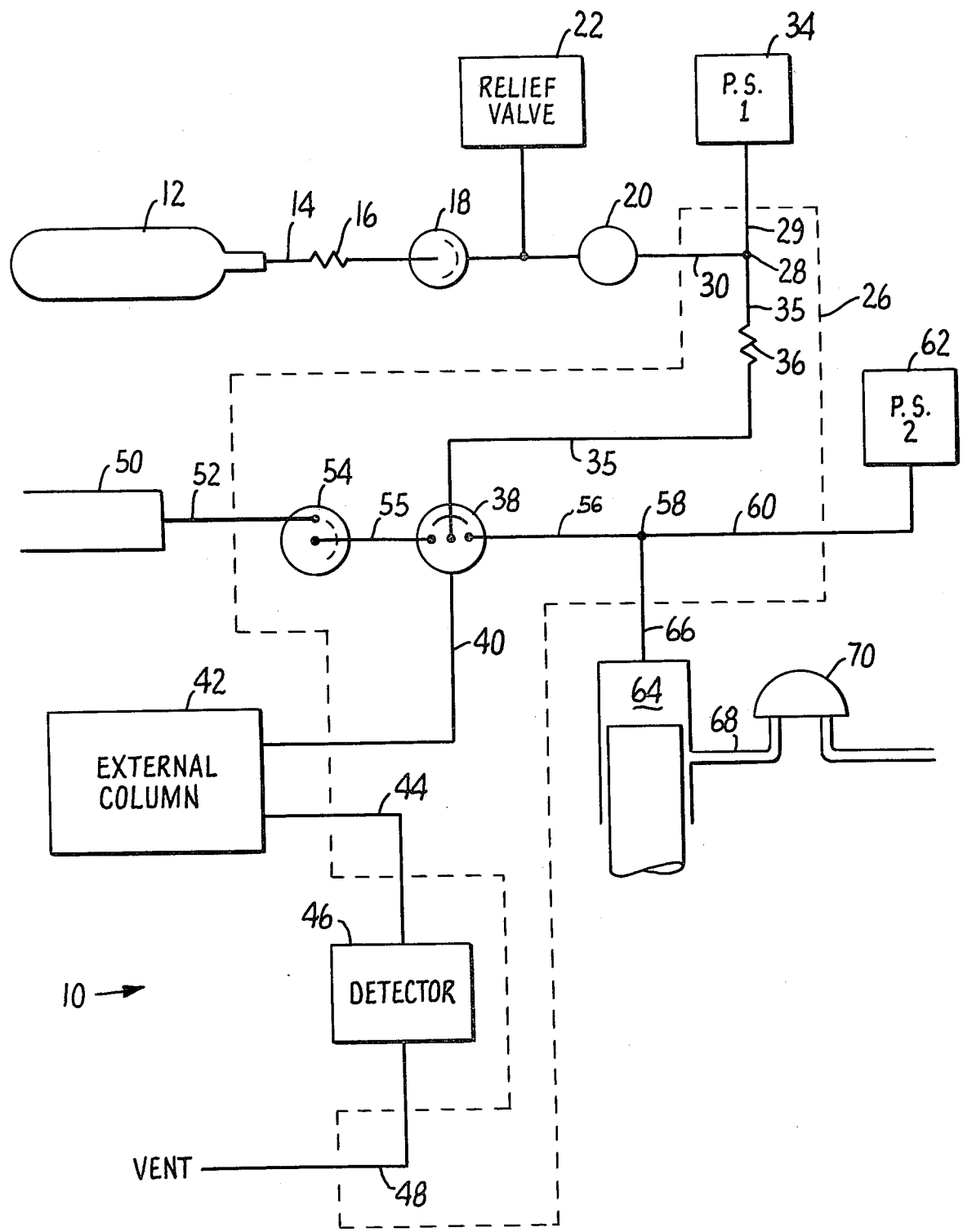
FIG. 1 is a schematic diagram of a gas chromatography system with the assembly of the present invention.

Referring to FIG. 1, there is shown a schematic view of a miniature gas chromatography system, generally designated as 10. The system 10 comprises a helium supply tank 12, which provides a carrier gas for the system 10. The carrier gas leaves the supply tank 12 and enters a line 14. The line 14 has disposed therein a restrictor 16, which is used to reduce the flow volume of the carrier gas. The carrier gas passes through the restrictor 16 to a first valve 18. From the first valve 18, the carrier gas is entered into a surge tank 20. The carrier gas, from the first valve 18, also enters into to a relief valve 22. The relief valve 22 is used to relieve any pressure over that which is necessary for charging the surge tank 20. Carrier gas from the surge tank 20 is entered into the carrier gas input 28 of the assembly 26 of the present invention.

The assembly 26 of the present invention is comprised of a substrate wafer 102, which has grooves etched therein. A typical material for the wafer 102 is single crystalline silicon. A plate 104, typically Pyrex glass, is attached to one side 103 of the wafer 102 and cooperates with the wafer 102 and the grooves therein to form gas channels. On the other side 105 of the plate 104 is a support 106. Typically, the support 106 is made of aluminum. The surge tank 20 is in the aluminum support 106. A conduit 30 passes through the plate 104, connecting the surge tank 20 to the carrier gas input 28. From the helium input 28, a first channel 29 is etched in the wafer 102 on the one side 103. The other end of the first channel 29 is connected to a first pressure sensor 34, which is used to determine the proper operating pressure for the carrier gas within the assembly 26. The first pressure sensor 34 is external to the assembly 26 and is mounted on the assembly 26. The first pressure sensor 34 is mounted on the other side 107 of the wafer 102 and is connected to the first channel 29 by a feedthrough. A second channel 35 within the wafer 102 connects the helium input 28 to a second valve seat 38. Within the second channel 35 is a second restrictor 36, the function of which will be described hereinafter.

From the second valve seat 38, one end of a third channel 40 is connected. The other end of the third channel 40 is connected to an external column 42. From the external column 42 a fourth channel 44 connects it to a detector 46. A fifth channel 48 in the assembly 26 connects the detector 46 to a vent.

A source 50 provides the sample gas to be analyzed in the gas system 10. The sample gas enters the assembly 26 through a sixth channel 52 and into a third valve seat 54. A seventh channel 55 connects the third valve seat 54 to the second valve seat 38. From the second valve seat 38, the sample gas passes through an eighth channel 56 to a pump connection point 58. At the pump connection point 58, a high pressure pump 64 is connected thereto. The high pressure pump 64 has an inlet 66 and an outlet 68. The inlet 66 of the high pressure pump 64 is connected to the pump connection point 58. The outlet 68 of the high pressure pump 64 is connected to a diaphragm vacuum pump 70. The diaphragm vacuum pump 70 draws the sample gas from the high pressure pump 64 and sends it out to vent. A ninth channel 60 connects the pump connection point 58 to a second pressure sensor 62.

The second and third valve seats 38 and 54, respectively, are of the types shown and described in the report prepared under the National Institute for Occupational Safety and Health, as set forth in the Background of the Invention. A second and third valve actuating means 38a and 54a (shown in FIGS. 4 and 5, respectively) are mounted on the second and third valve seats 38 and 54, respectively. The first valve 18 can also comprise a valve actuator operating on a valve seat, similar to the second valve actuator 38a on the second valve seat 38. The valve actuating means 38a and 54a will be described in greater detail hereinafter, and are attached to the substrate wafer 102 on the other side 107 thereof. Also attached to the other side 107 of the substrate 102 is the first pressure sensor 34, the second pressure sensor 62, the pump 64, the external column 42 and the detector 46. Feedthroughs in the substrate wafer 102 communicate each of the aforementioned external devices with the channels which are etched on the one side 103 of the wafer 102. The detector 46 can be of the type described in the patent application Ser. No. 141,269, filed on Apr. 18, 1980, now abandoned. The first and second pressure sensors 34 and 62, respectively, can be of commercially available type of sensor, such as Kulite Semiconductor Inc. Model PTQH. The external column 42 can also be of a commercially available type of column, such as the fused silica capillary column manufactured by Hewlett-Packard Corporation. The pump 64 used in the assembly 26 will be described in detail hereinafter.

In normal operations, the carrier gas will flow from the tank 12 through the first valve 18 and into the surge tank 20. Once the surge tank 20 has been charged or pressurized, the first valve 18 is closed. Thereafter, the carrier gas will flow from the surge tank 20, through the conduit 30 into the second channel 35, through the restrictor 36 therein. The carrier gas then flows through the second valve seat 38, through the third channel 40 to the external column 42. The carrier gas will then re-enter the assembly 26 from the external column 42 and pass through the fourth channel 44 to a detector 46 and through a fifth channel 48 to vent. During normal operation, the sample gas will travel from the source 50, through a normally open third valve seat 54, through the second valve seat 38 into the inlet 66 of the pump 64.

From the pump 64, the sample gas is drawn through the outlet 68 of the pump 64 by the diaphragm vacuum pump 70 and to vent 72. The diaphragm vacuum pump 70 draws the sample gas from the sample gas channel line (i.e. sixth, seventh and eighth channels 52, 55, and 56 respectively) out to vent. The vacuum action of the pump 70 draws in new sample gas from the source 50 into the sample gas channel line.

When it is desired to inject sample gas into the carrier gas line for testing by the external column 42, the third valve seat 54 is closed by the third valve actuating means 54a, thereby shutting the flow of sample gas from the source 50. The pump 64 is activated. When the pressure in the seventh, eighth and ninth channels, 55, 56, and 60, respectively, as measured by the second pressure sensor 62 is greater than the pressure in the first and second channels 29 and 35, respectively, as measured by the first pressure sensor 34 by a pre-determined amount, the second valve actuating means 38a which is seated on the second valve seat 38 is then operated to permit the sample gas from the eighth channel 56 to enter into the carrier gas line. The second valve seat 38 is opened for a pre-determined amount of time (typically on the order of a few milliseconds). During the injection of the sample gas from the eighth channel 56, the sample gas enters through the second valve seat 38 and into the second and the third channels 35 and 40, respectively, of the carrier gas line. The second restrictor 36 in the second channel 35 prevents the sample gas from flowing upstream into the surge tank 32 to contaminate it. Therefore, although some sample gas will enter into the second channel 35, substantially all of the sample gas from the eighth channel 56 will be injected into the third channel 40, into the external column 42 and will be measured by the detector 46.

To eliminate the problem of pump contamination, i.e., gas from within the pump 64 entering into the carrier gas line and the external column 42, the volume of the eighth channel 56 is chosen such that it acts as a buffer between the sample gas from the pump 64 and the second valve seat 38. In particular, the volume of the eighth channel 56 is such that, upon activation of the pump 64, no sample gas which has been in the pump 64 reaches the second valve seat 38. The volume of the eighth channel 56 must be greater than the compression ratio of the pump 64 times the volume of the gas which is in the second valve seat 38, seventh channel 55 and that portion of the third valve seat 54 which is in communication with the seventh channel 55 and is not closed by the third actuator 54a. In this manner, contamination of gas from the pump 64 into the carrier gas line is avoided.

As soon as the second actuator 38 returns to its normally closed position, the pump 64 stops its injection process and withdraws to its normal open position permitting gas flow from the inlet 66 to the outlet 68. Third valve seat 54 is then opened permitting sample gas to flow from the source 50 to the pump 64, and out to vent by the diaphragm pump 70.

With the external column 42 exterior to the wafer 104, the manufacturing of gas chromatography systems 10 for different applications is greatly eased. The external column 42 contains chemical means for the separation of the sample gas mixture into its constituent components. For analysis of different sample gases in different applications, the external column 42 may have to be different. However, the assembly 26 for the different applications can all be the same. Thus, for analyzing different gases, the different external columns 42 can be attached to the same assembly 26 for various applications. In this manner, only the external column 42 is different for different uses. Commonality of parts with decrease in inventory stock result in savings in manufacturing cost.

Figure 2:
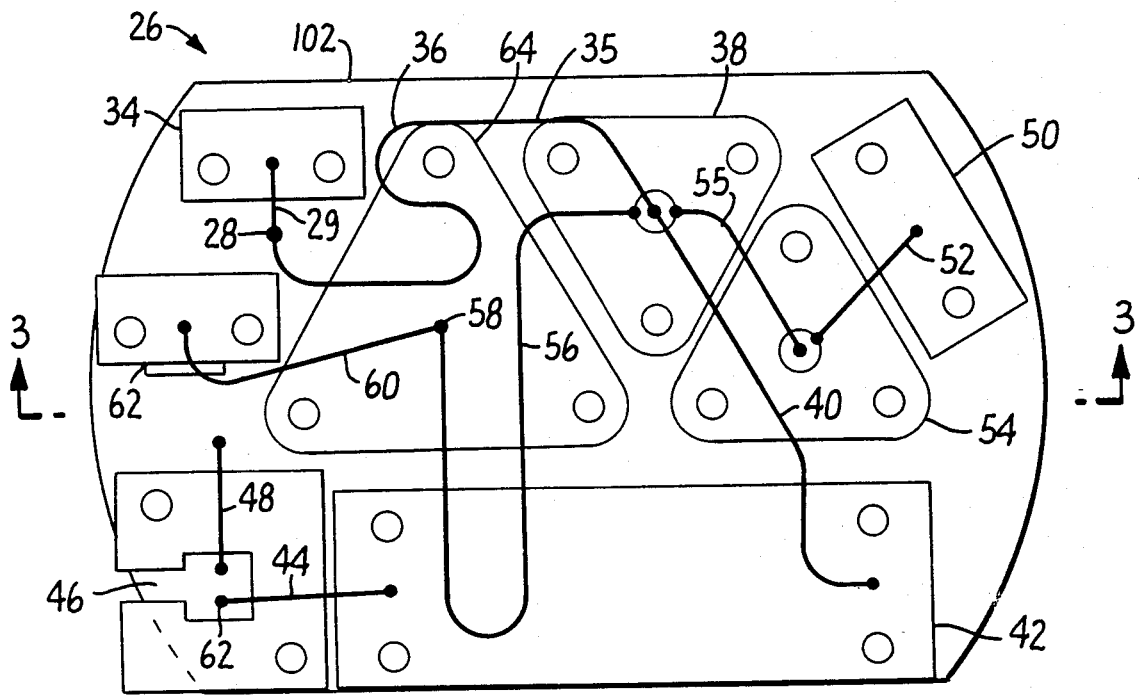
FIG. 2 is a footprint of the gas chromatography assembly of the present invention.
Figure 3:
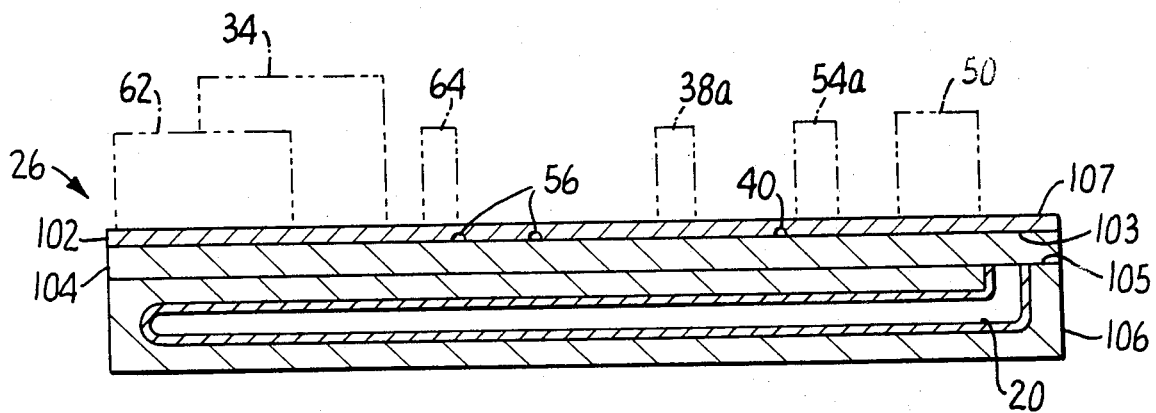
FIG. 3 is a cross-sectional view of the assembly of FIG. 2 taken along the line 3—3.
Figure 4:
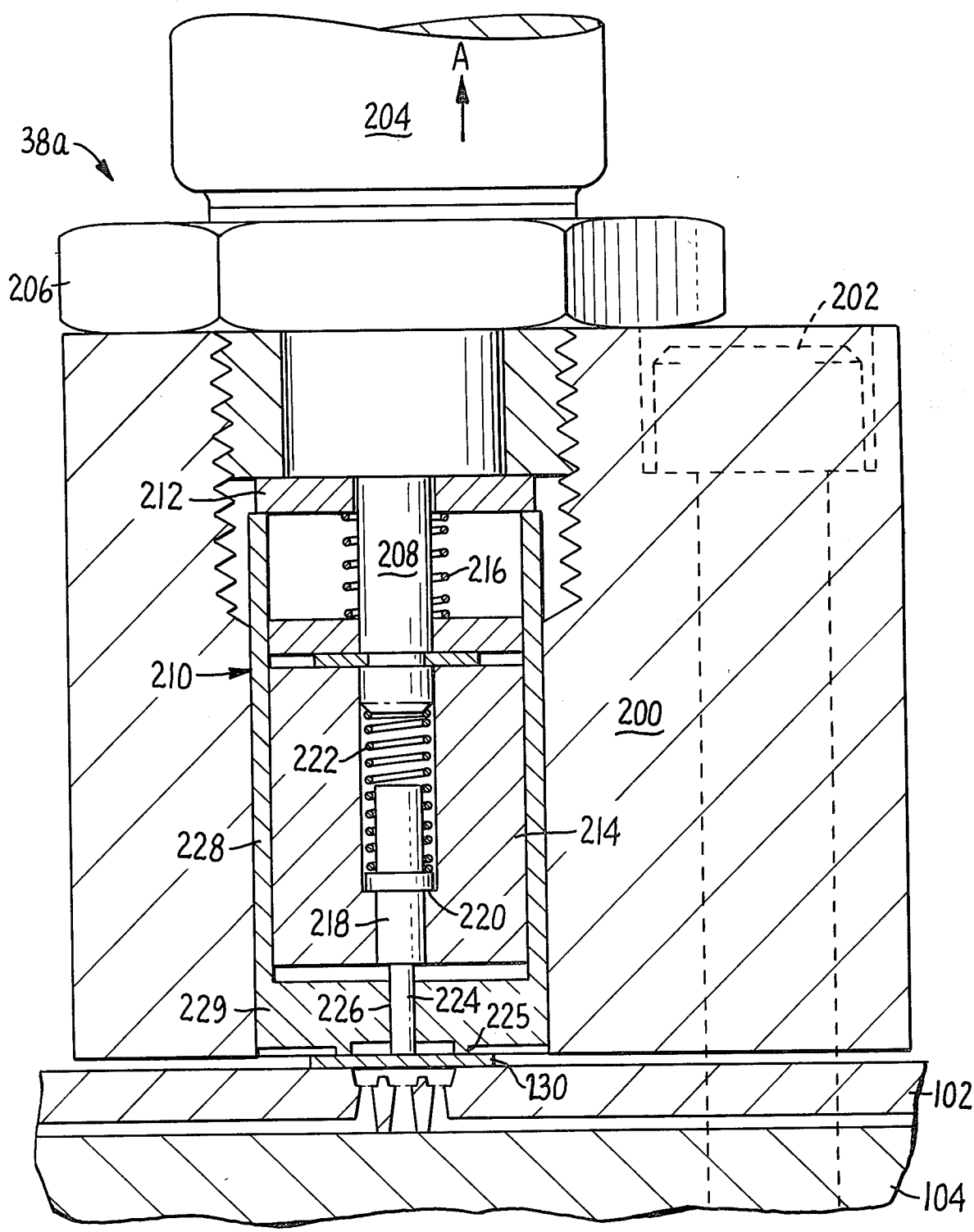
FIG. 4 is a partial cross-sectional view of a normally closed valve actuator used in the assembly of the present invention.

Referring to FIG. 4, there is shown a partial cross-sectional view of the second valve actuator 38a, used in the assembly 26 of the present invention. The valve actuator 38a consists of a housing 200, with the housing 200 connected to the silicon wafer 102, plate 104 and support 106 by bolt 202. As shown in FIG. 2, there are three bolts 202 attaching the actuator 38a to the valve seat 38. Disposed above the housing 200 is an electrically operated solenoid 204, which is used to activate the valve 200 when desired. The solenoid 204 threadably engages the housing 200, and is locked into place by a nut 206.

The housing 200 has disposed therein a valve assembly 210. The valve assembly 210 is bound securely in the housing 200 between the silicon wafer 102 and the solenoid 204. The assembly 210 has disposed therein a sleeve 228 with an end 229. The sleeve 228 has an orifice 226 in the end 229 thereof. A pin 224 is within the orifice 226. A circular ring 225 is at the outer surface of the end 229. The ring 225 engages the diaphragm 230 and when the solenoid 204 is threadably tightened, the ring 225 is pressed against the diaphragm 230 and the wafer 102 forming a tight seal.

The sleeve 228 also has disposed therein a first plunger 208. The first plunger 208 slides through a first annular ring 212. The first annular ring 212 is clamped between the solenoid 204 and the sleeve 228. The first plunger 208 is mounted in the solenoid 204, such that upon activation of the solenoid 204, the first plunger 208 is moved in the direction shown by the arrow A. At the end of the first plunger 208 which is within the sleeve 228 is a body 214. A first spring 216 is between the body 214 and the first annular ring 212. The first spring 216 urges the body 214 away from the solenoid 204.

Within the body 214 is a second plunger 218. The body 214 has a lip 220 therein which captures the second plunger 218. A second spring 222 is also within the body 214. The second spring 222 urges one end of the second plunger away from the first plunger 208. At the other end of the second plunger 218, the plunger 218 is in free contact with the pin 224. The pin 224 is aligned to impinge the diaphragm 230. The diaphragm 230 controls the flow of gas through the valve seat 38. The pin 224 is aligned to move in a direction substantially perpendicular to the plane of the diaphragm 230.

In the operation of the valve actuator 38a, when solenoid 204 is not activated, the first spring 216 urges the body 214 away from the solenoid 204 until the shoulder on the plunger 208 stops against the ring 212. Similarly, the second spring 222 urges the second plunger 218 away from the first plunger 208. The action of the second spring 222 against the second plunger 218 causes the second plunger 218 to impinge the pin 224, pushing it against the diaphragm 230, closing off the gas flowing to the valve seat 38.

When the solenoid 204 is activated, the first plunger 208 is pulled in a direction shown substantially by the arrow A. The first plunger 208 pulls the body 214 with it in the direction as shown by the arrow A. As the body 214 moves in the direction of "A", the lip 220 of the body 214 pulls the second plunger 218 also in the direction shown by the arrow A. The effect of solenoid 204 pulling on the first plunger 208 is then to compress the first spring 216. The pin 224, however, is only in free contact with the second plunger 218. The pin 224 moves in the direction shown by the arrow A only due to the springlike resilient restoring force of the diaphragm 230 and by the force of the gas pushing against the diaphragm 230.

When the solenoid is deactivated, the spring action of the first spring 216 pushes the body 214 away from the solenoid 204. As the bottom end of the plunger 218 impinges upon pin 224, the plunger 218 stops its movement in the direction opposite to that shown by arrow A and disengages from the lip 220 of the body 214. Spring 222 is compressed by the further movement of plunger 218 in the direction opposite shown by arrow A. The force of the second spring 222, pushing against the second plunger 218, also pushes the pin 224 against the diaphragm 230 to close off the valve seat 38.

As can be seen from the foregoing description, in the absence of the force of activation by the solenoid 204, the valve seat 38 is normally closed to the flow of gas. Moreover, the pin 224 which impacts the diaphragm 230 to open or close the valve 38 is moved by the valve assembly 210 only in the direction opposite to that shown by the arrow A. When the solenoid 204 is activated, moving the valve assembly 210 away from the pin 224, the pin 224 is moved in the direction opposite to that shown by the arrow A only by the diaphragm 230 and the force of gas flowing through the valve seat 38.

The function of the valve assembly 210 is to act as a force-transmitting means, such that during the closing of the valve seat 38, a gentle and gradual force is applied on the pin 224. In fact, the force which is applied against the pin 224 to close off the valve seat 38 is applied by the force of the second spring 222. The second spring 222 can be made to apply a very gentle and gradual force, such as on the order of 50 grams of force. Gradual and gentle forces are needed because sudden forces applied against the pin 224 can cause breakage of the pin 224 and/or greatly deteriorate the life of the diaphragm 230 when the diaphragm is repeatedly and suddenly struck by the pin 224 and impinged against the wafer 102. Finally, because the orifice 226 in which the free pin 224 is situated is part of the housing 200, and the housing 200 is aligned substantially perpendicular to the diaphragm 230, and the wafer 102, the pin 224 would also be aligned substantially perpendicular to the diaphragm 230 and the wafer 102. This provides greater accuracy in the operation of the valve 38a.

Figure 5:
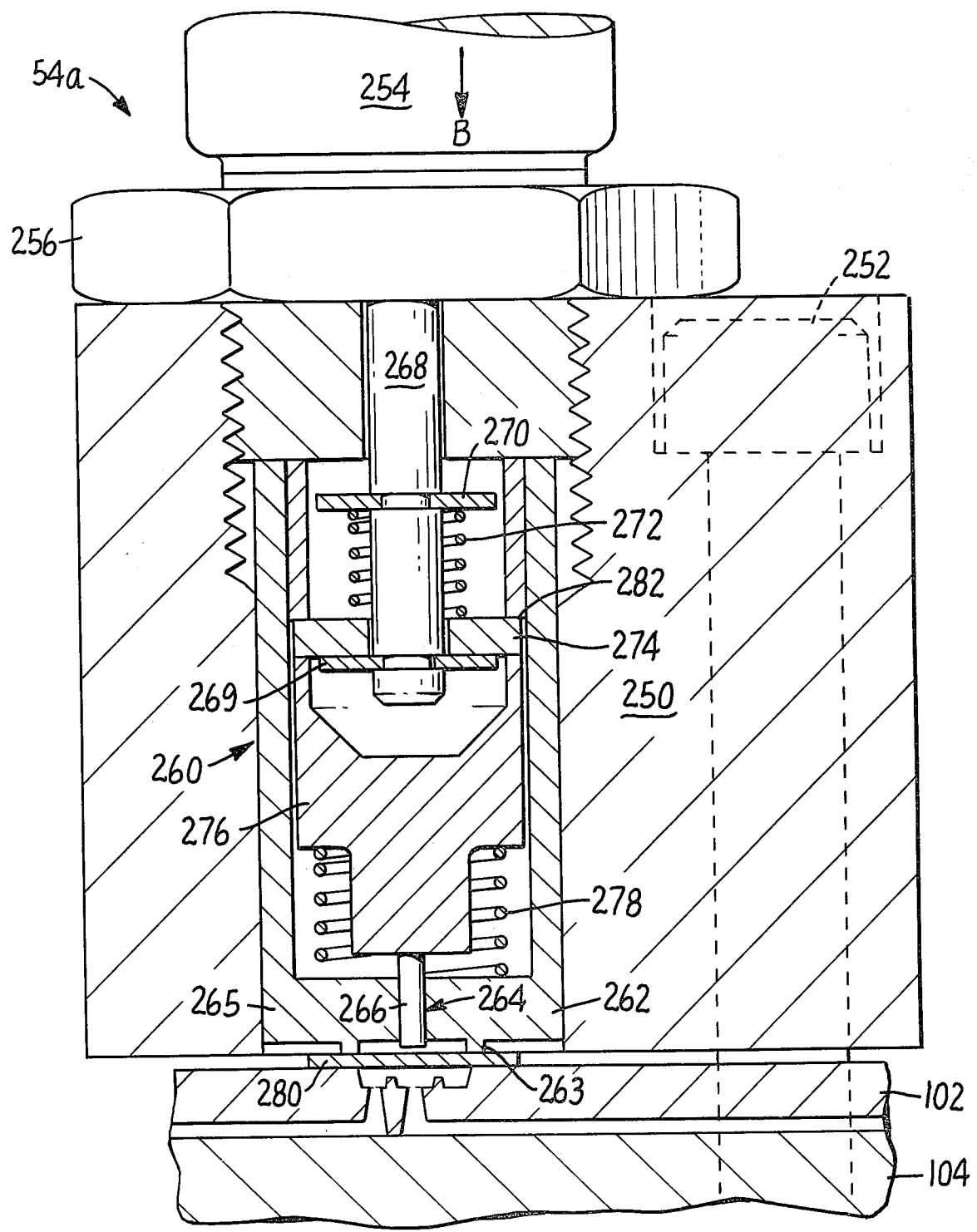
FIG. 5 is a partial cross-sectional view of a normally open valve actuator used in the assembly of the present invention.

Referring to FIG. 5, there is shown a partial cross-sectional view of the third valve actuator 54a used in the assembly 26 of the present invention. The valve actuator 54a consists of a housing 250, with the housing 250 connected to the silicon wafer 102, the plate 104 and the support 106 by bolts 252. Again, as shown in FIG. 2, there are three bolts 252 attaching the valve actuator 54a to the assembly 26. Disposed above the housing 250 is an electrically operated solenoid 254 which is used to activate the valve 54a when desired. The solenoid 254 threadably engages housing 250 and is locked into place by a nut 256.

The housing 250 has disposed therein a valve assembly 260. The valve assembly 260 is bound securely in the housing 250 between the silicon wafer 102 and the solenoid 254. The assembly 260 has disposed therein a sleeve 262. This sleeve 262 is similar to the sleeve 228 described for the second valve actuator 38a, as shown in FIG. 4. The sleeve 262 has an orifice 264 at one end 265 thereof. A free pin 266 is disposed within the orifice 264. The housing 250 is attached to the wafer 102, plate 104, and support 106, such that the orifice 264 and, therefore, the pin 266 is in substantially perpendicular alignment with the diaphragm 280 of the valve seat 54. The sleeve 262 also has a circular ring 263 which engages the diaphragm 280. When the bolts 252 are tightened, the circular ring 263 is pressed against the diaphragm 280 and against the wafer 102 forming a tight seal for the valve seat 54.

Within the valve assembly 260 is a first plunger 268. The first plunger 268 extends through the valve assembly 260 into the solenoid 254. Upon activation of the solenoid 254, the first plunger 268 is moved in the direction shown by the arrow "B". A first ring 270 is attached around the first plunger 268 near the solenoid 254. A second ring 274 is attached around the plunger 268 by E-ring 269 near the end of the plunger 268, away from the solenoid 254. A first spring 272 is disposed between the first ring 270 and the second ring 274 and is always in compression. The second ring 274 is in contact with one end of a cylindrical body 276. The other end of the cyclindrical body 276 is in free contact with the pin 266. A second spring 278 is disposed around the other end of the cyclindrical body 276 and urges the body 276 away from the one end 265 of the sleeve 262. The action of the second spring 278 is to urge the body 276 against the second ring 274. The body 276 is urged against the second ring 274 until the second ring 274 comes to a rest against the stop 282.

In the operation of the actuator 54a, when the solenoid 254 is activated, the plunger 268 is moved in the direction shown by the arrow B. The movement of the plunger 268 pushes the first ring 270 thereby compressing the spring 272. The spring 272 then pushes against the second ring 274. The force of the first spring 272 is then transmitted to the cylindrical body 276. This force, i.e., the force of the first spring 272, then works against the force of compression of the second spring 278. Therefore, the amount of force acting on cylindrical body 276 is the difference in force between the first spring 272 and the second spring 278. This force acting on the body 276 is then transmitted to the pin 266. The pin 266 impinges against the diaphragm 280 closing off the flow of gas through the valve seat 54.

When the solenoid 254 is de-energized, the force of the second spring 278 would urge the cylindrical body 276 upward, i.e., in the direction opposite to that shown by the arrow B. The body 276 would then urge against the second ring 274 pushing the plunger 268 back into the state shown in FIG. 5. The pin 266 is in free contact with the one end of the body 276. The pin is retracted and is moved in a direction opposite to that shown by the arrow B by the springlike force of the diaphragm 280, returning to its normal position. Therefore, the pin 266 is affected by the force of activation of the valve actuator 54a in only the direction shown by the arrow "B". The restoration of the pin 266 to its normal state is not directly caused by the de-energization of the solenoid 254.

Similar to the description for the actuator 38a shown in FIG. 4, the function of the valve assembly 260 is to act as a force transmitting means such that during the activation of the solenoid 254, a more gentle and gradual force is applied on the pin 266, and consequently against the diaphragm 280. The amount of force applied against the pin 266 is the difference in the spring compression between the first spring 272 and the second spring 278. This difference can be adjusted such that the amount of force applied against the pin 266 can be extremely gradual and gentle. Finally, because the orifice 264 in which the pin 266 is situated is part of the housing 250, the housing 250 can be aligned substantially perpendicular to the diaphragm 280 and the wafer 102 providing accuracy in the operation of the valve 54a.

Figure 6:
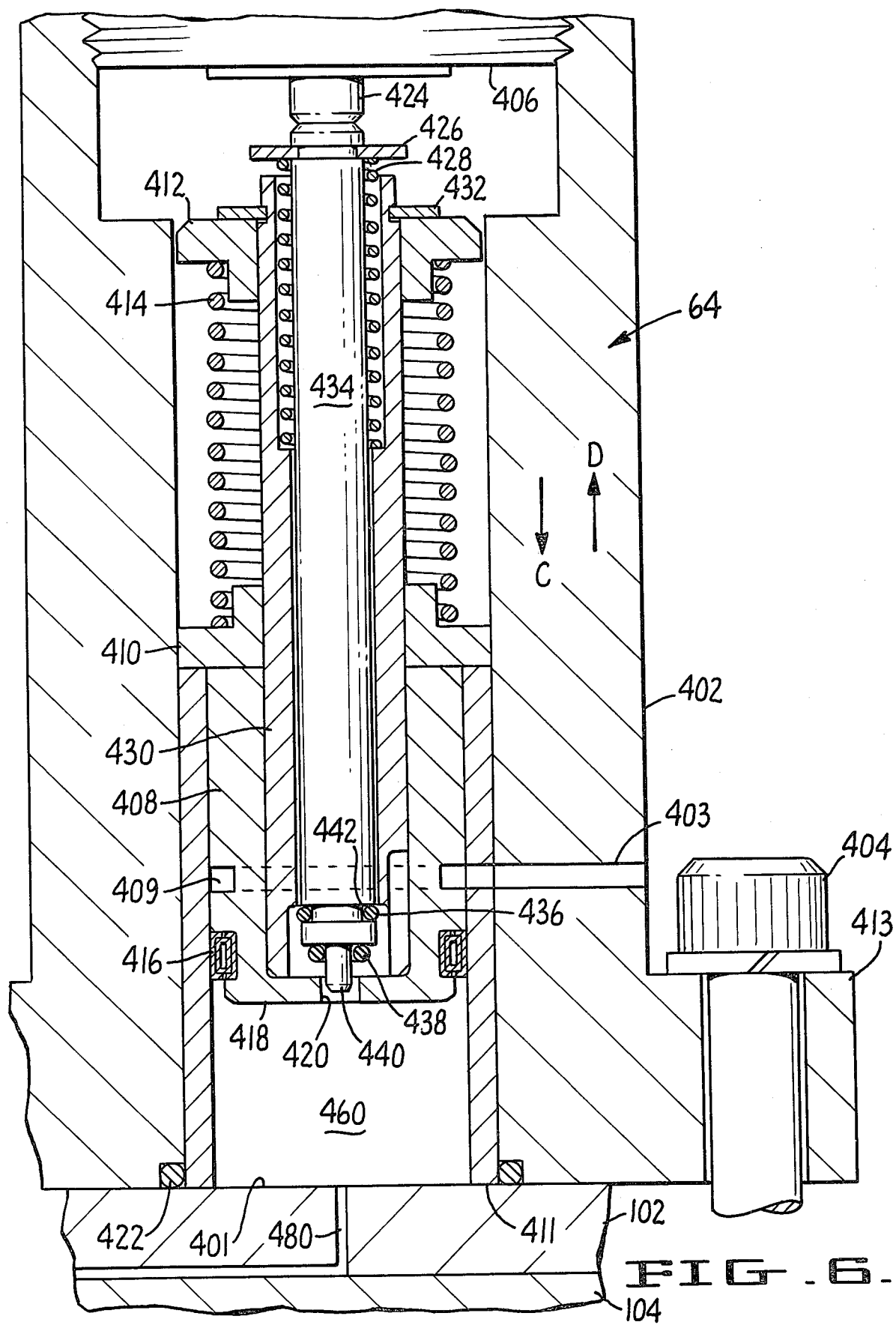
FIG. 6 is a partial cross-sectional view of the injection pump used in the assembly of the present invention.

FIG. 6 shows a partial, cross-sectional view of a high-pressure injection pump 64 used in the assembly 26 of the present invention. The pump 64 has a housing 402. The housing 402 is attached to the wafer 102, the plate 104, and the aluminum support 106 by a bolt 404. As shown in FIG. 2, there are three bolts 404 attaching the pump 64 to the assembly 26. The housing 402 has an orifice 403 for connection to a diaphragm vacuum pump 70. Threadably connected to the housing 402 is a solenoid 406. The solenoid 406 has an operable member 424 which is used to actuate the pump 64. Inside the housing 402 is a glass tube 411.

A piston 408 is disposed within the glass tube 411. The piston 408 is prevented from any upward movement past the glass tube 411 by spring stops 410. Piston 408 has an annular groove 409 which is aligned with orifice 403 of housing 402 to allow sample gas flow to the diaphragm vacuum pump 70 during normal operations, when sample gas is not being injected into the external column 42. The piston 408 also has seals 416 to prevent flow of gas between the piston 408 and the glass tube 411. The piston 408 has a base 418, which has an aperture 420 therein.

The piston 408 also has a bore, which has affixed therein a valve guide 430. The valve guide 430 is threaded on to the piston 408 and extends upward between the base 418 of the piston 408 up to the solenoid operable member 424. The upper portion of the valve guide 430 has an annular groove which has therein disposed a spring retainer 432. The spring retainer 432 impinges upon the nylon shoulder washer 412 which, with spring stop 410, provide spring retainer means for the spring 414.

Within the valve guide 430 is a valve plunger 434. The valve plunger 434 extends from the operable portion 424 of the solenoid 406 down to the base 418. Near the base of the valve plunger 434 is an annular groove 442 which has disposed thereon sealing O-ring 436. The O-ring 436 prevents the flow of gas past the O-ring 436 such that gas will not enter between the valve guide 430 and valve plunger 434. The end of the valve plunger 434 has an end 440. Disposed about the end 440 is a second O-ring 438. The end 440 and the second O-ring 438 can be sealably engaged with the orifice 420. At the other end of the plunger 434 is a bore which has disposed therein second spring 428. The second spring 428 is retained in its position by the annular ledge of the bore and by an E-ring 426.

The valve guide 430 near the base 418 of the piston 408 has a portion cut-out such that the gas flow through the aperture 420 past the base portion of the valve plunger 434, and through the annular groove 409 of the piston 408 and out the orifice 403 of the housing 402.

When the pump 400 is in operation, the solenoid 406 is activated and the operable member 424 will move in a direction "C" which will move the plunger 434 down a discrete amount until the second O-ring 438 engages and then seals the orifice 420. At this point, the gas from the wafer 102 is sealed off from communication with the orifice 403 of the housing 402. As the operable member 424 proceeds further in the direction shown by the arrow C, and since the valve plunger 434 is against the base 418 of the piston 408, the downward movement of the entire valve guide 430 will cause the piston 408 to move in the direction shown by the arrow C. The piston 408 then separates from the spring stop 410. Additionally, the springs 414 will be compressed during this downward motion. The movement of the entire piston assembly 408 causes the gas in the chamber 460 to be compressed and to be injected into the wafer 102.

The compression of the gas within the chamber 460 will cause the pressure of the gas to increase. Seals 416 and O-rings 438 and 422 prevent the gas within the chamber 460 from communicating with the outside atmosphere. The downward action of the piston 408 continues until the pressure of the gas in the chamber 460 and in channel 56 is higher than the pressure of the carrier gas in channels 35 and 40 in the wafer 102. With the second valve 38 opened, this permits the injection of the sample gas into the carrier gas line. The solenoid 406 will push the piston 408 in the direction shown by the arrow C until the solenoid 406 reaches its limit. The piston 408 then stops. The amount of travel of the piston 408 can be adjusted by the amount of threading of the solenoid 406 to the housing 402. This in turn adjusts the compression ratio of the pump 64.

To inactivate the pump 64, the solenoid 406 is de-energized. Spring 414 will then push the piston 408 back up against spring stop 410. The spring 414 will also position the nylon shoulder washer 412 to the position shown in FIG. 6. In addition, spring 428 will bias against the annular bore within the valve guide 430 and bias the operable portion 424 back to its original position, lifting the end of the valve plunger 434 from the base 418 of the piston 408. This opens up the aperture 420. At this time, there will be a gas passage from the wafer 102 through the feedthrough 480 into the chamber 460, through the orifice 420, through the annular groove 409, and through the orifice 403 to the vacuum pump 70. O-ring 436 forms a seal between the plunger 434 and the bore 430.

Referring to FIG. 7, there is shown a partial cross-sectional side view of a coupling device 500 for attaching the external column 42 to the silicon wafer 102, glass plate 104, and the support 106. The coupling device 500 has a housing 502 and is connected to the wafer 102, plate 104 and support 106 by bolts 504. There are four bolts 504 attaching the external column 42 to the assembly 26. The housing 502 has a sleeve 508 which is inserted into a feedthrough 522 in the wafer 102. The sleeve 508 has an end 524 which extends into the feedthrough 522. An O-ring 520 is disposed in an annular groove around the sleeve 508. The O-ring 520 is in contact with the other side 107 of the wafer 102. Although the end 524 extends into the wafer 102, there is not enough volume in the feedthrough 522 in which it extends such that it will create a dead volume problem of gas remaining in the feedthrough 522. The external column 42 has a coupling end 506, which fits within the sleeve 508. A sealing material, such as epoxy glue, seals the end 506 within the sleeve 508. The bolts 504 assertably engages the external column 42 with the housing 502, and extends the sleeve 508 into the feedthrough 522 of the wafer 102. The O-ring 520 forms a tight seal.

What is claimed is:

1. A miniature gas chromatography assembly comprising
    a substrate wafer having:
        an etched carrier gas groove means for containing carrier gas;
        an etched sample gas groove means for containing sample gas; and
        a first valve seat means, said sample gas groove means and said carrier gas groove means passing through said first valve seat means;
    a plate cooperating with said wafer and said groove means to define gas channel means;
    a first valve actuating means attached to said first valve seat means for controlling the flow of sample gas from said sample gas channel means into said carrier gas channel means;
    a pump means attached to said wafer connected to said sample gas channel means; said pump means cooperating with said first valve actuating means for injecting sample gas from said sample gas channel means into said carrier gas channel means;
    a modular capillary tube means attached to said wafer; one end of said capillary tube means connected to said carrier gas channel means; and
    a detector means connected to other end of said capillary tube means for measuring properties of gas flowing from said capillary tube means.

2. In a miniature gas chromatography assembly having
    an etched carrier gas channel means for containing carrier gas;
    an etched sample gas channel means for containing sample gas;
    a first valve means;
    said carrier gas channel means and said sample gas channel means passing through said first valve means;
    said first valve means for controlling the flow of sample gas from said sample gas channel means into said carrier gas channel means;
    a capillary tube means connected to said carrier gas channel means and
    a detector means connected to said capillary tube means for measuring properties of gas flowing from said capillary tube means, wherein the improvement comprising:
        a pump means connected to said sample gas channel means; said pump means cooperating with said first valve means for injecting gas from said sample gas channel means through said first valve means into said carrier gas channel means; and
        wherein the volume of said sample gas channel means between said first valve means and said pump means is such that no gas from said pump means is injected into said carrier gas channel means.

3. The assembly of claim 2 wherein said first valve means comprises a first valve seat means and a first valve actuating means.

4. The assembly of claim 3 wherein said carrier gas channel means, said first valve seat means and said sample gas channel means are all in a substrate body.

5. The assembly of claim 4 wherein said substrate body comprises a substrate wafer having grooves etched therein and a plate cooperating with said wafer and said grooves to define gas channels.

6. The assembly of claims 1 or 5 further comprising:
    a second valve seat means, said sample gas channel means passing through said second valve seat means;

a second valve actuating means attached to said second valve seat means for controlling the flow of sample gas through said second valve seat means and into the first valve seat means.

7. The assembly of claim 6 wherein said first and second valve actuating means each comprises:
   a housing with a guide;
   a pin means in said guide;
   a diaphragm for controlling the flow of gas through the valve seat means to which said actuating means is attached;
   said pin means aligned to move in one direction in said guide to impinge said diaphragm;
   a plunger means for moving in said one direction to impinge said pin means; and
   said pin means in free contact with said plunger means, whereby said pin means is moved by said plunger means only in said one direction.

8. The assembly of claim 7 wherein said housing is attached to said wafer such that said guide is substantially perpendicular to said wafer.

9. The assembly of claim 8 wherein said plunger means further comprises:
   a force activation means;
   a resilient force transmission means;
   said force transmission means in free contact with said pin means; and
   said force activation means for imparting a force to said resilient force transmission means.

10. The assembly of claim 9 wherein said force activation means is an electrically operated solenoid.

11. The assembly of claim 10 wherein said pin means is a pin.

12. The assembly of claim 11, wherein said first actuating means is a normally closed actuating means whereby in the absence of activation of said solenoid, sample gas is prevented from flowing into the carrier gas channel means.

13. The assembly of claim 12, wherein said solenoid is adapted to impart a force to said resilient force transmission means in a direction opposite to said one direction.

14. The assembly of claim 13, wherein said force transmission means further comprising
   a body, one end of said body for activation by said solenoid;
   a first spring, said first spring urging said body away from said solenoid;
   a stem; one end of said stem in free contact with said pin;
   a second spring; and
   said stem and said second spring in said body; said second spring urging said stem against said pin and away from the other end of said body;
   whereby the force on said pin is supplied by said second spring.

15. The assembly of claim 11, wherein said second actuating means is a normally open actuating means, whereby in the absence of activation of said solenoid, sample gas can flow through said second valve seat means.

16. The assembly of claim 15, wherein said solenoid is adapted to impart a force to said resilient force transmission means in said one direction.

17. The assembly of claim 16, wherein said force transmission means further comprising:
   a stem; one end of said stem for activation by said solenoid;
   a first spring; said stem biased against said first spring;
   a body; one end of said body in free contact with said pin;
   a second spring; said second spring urging said body away from said pin and against said stem,
   whereby upon activation of said solenoid, the force on said pin is supplied by the difference in force between said first spring and said second spring.

18. The assembly of claims 1 or 2 wherein said pump means comprises
   a housing with an inlet and an outlet;
   said inlet connected to said sample gas channel means;
   a gas passage from said inlet to said outlet;
   a piston assembly disposed in said housing for injecting gas in said pump through said inlet;
   a valve assembly disposed in said piston assembly for closing said gas passage; and
   actuating means for moving said valve assembly to close said gas passage and then for moving said piston assembly to inject said gas.

19. The assembly of claim 18 wherein said piston assembly comprises a piston having a bore, an opening in the base of said piston, and an annular groove in the outer periphery of the piston wall;
   said valve assembly in said bore; and
   said passage formed by said inlet in communication with said opening, said annular groove and said outlet.

20. The assembly of claim 19 wherein said valve assembly comprises a valve plunger; one end of said plunger for sealably engaging the opening in the base of said piston.

21. The assembly of claim 1 or 5 further comprising a coupling device for fitting said capillary tube means to said wafer, said device comprising:
   a housing having a bore for receiving said tube in one end;
   another end of said bore in said wafer connected to said gas channel; and
   sealing means around said another end of said bore for reducing dead volume in said wafer.

22. The device of claim 21 wherein said sealing means is an O-ring.

23. A method of analyzing sample gas in a miniature gas chromatography apparatus comprising the steps of:
   flowing said sample gas in one direction in an etched sample gas channel past an injection site to a pumping site;
   pumping said sample gas at said pumping site in a direction opposite said one direction to said injection site;
   injecting said pumped sample gas into an etched carrier gas channel at said injection site;
   buffering said pumped sample gas such that no gas from within said pump is injected into said carrier gas channel; and
   analyzing said sample gas in said carrier gas channel.

24. A miniature gas chromatography assembly comprising a substrate wafer having:
   an etched carrier gas groove means for containing carrier gas;
   an etched sample gas groove means having an inlet and an outlet for containing sample gas; and
   a first valve seat means, said sample gas groove means and said carrier gas groove means passing through said first valve seat means;
   a plate cooperating with said wafer and said groove means to define gas channel means;

a vacuum pump means connected to the outlet of said sample gas channel means; said pump means for drawing sample gas through said channel means;

means for injecting said sample gas from said sample gas channel means into said carrier gas channel means;

a modular capillary tube means attached to said wafer; one end of said capillary tube means connected to said carrier gas channel means; and a detector means connected to other end of said capillary tube means for measuring properties of gas flowing from said capillary tube means.

* * * * *